US012734198B2

(12) United States Patent
Baik

(10) Patent No.: US 12,734,198 B2
(45) Date of Patent: Sep. 15, 2026

(54) COMPOSITION FOR PREVENTING, ALLEVIATING OR TREATING SLEEP DISORDERS, CONTAINING, AS ACTIVE INGREDIENT, GUT MICROBIOTA OR EXTRACELLULAR VESICLES DERIVED THEREFROM

(71) Applicant: Kookmin University Industry Academy Cooperation Foundation, Seoul (KR)

(72) Inventor: Inkyung Baik, Seoul (KR)

(73) Assignee: Kookmin University Industry Academy Cooperation Foundation, Seoul (KR)

( * ) Notice: Subject to any disclaimer, the term of this patent is extended or adjusted under 35 U.S.C. 154(b) by 339 days.

(21) Appl. No.: 18/275,480

(22) PCT Filed: Jan. 28, 2022

(86) PCT No.: PCT/KR2022/001667

§ 371 (c)(1),
(2) Date: Aug. 2, 2023

(87) PCT Pub. No.: WO2022/169254

PCT Pub. Date: Aug. 11, 2022

(65) Prior Publication Data

US 2024/0108665 A1 Apr. 4, 2024

(30) Foreign Application Priority Data

Feb. 3, 2021 (KR) ........................ 10-2021-0015295
Jul. 5, 2021 (KR) ........................ 10-2021-0087932
Jan. 26, 2022 (KR) ........................ 10-2022-0011607

(51) Int. Cl.

*A61K 35/741* (2015.01)
*A61K 9/127* (2025.01)
*A61K 35/00* (2006.01)
*A61P 25/00* (2006.01)

(52) U.S. Cl.

CPC ............ *A61K 35/741* (2013.01); *A61K 9/127* (2013.01); *A61P 25/00* (2018.01); *A61K 2035/115* (2013.01)

(58) Field of Classification Search

None
See application file for complete search history.

(56) References Cited

U.S. PATENT DOCUMENTS

2023/0355689 A1* 11/2023 Davitt .................. A61K 9/4891
2024/0066074 A1* 2/2024 Moiseyenko ........... A61P 25/16
2025/0114411 A1* 4/2025 Altaf ...................... A61K 47/46

FOREIGN PATENT DOCUMENTS

| | | | |
|---|---|---|---|
| CN | 110157647 | A | 8/2019 |
| KR | 10-2020-0121790 | A | 10/2020 |
| KR | 10-2020-0131657 | A | 11/2020 |
| WO | 2020/078718 | A1 | 4/2020 |
| WO | 2020161113 | A1 | 8/2020 |

OTHER PUBLICATIONS

Sleep Disorders from the Cleveland Clinic (https://my.clevelandclinic.org/health/diseases/11429-sleep-disorders, accessed online Jul. 21, 2025). (Year: 2025).*

Balakrishnan, et al., "Provotella histicola treatment reduces arthritic pain and partially normalizes gut microbiota and metabolites", Elsevier Journal of Immunology, May 1, 2020, vol. 204, pp. 1-2 (2 pages).

Gary D. Wu et al., "Linking Long-Term Dietary Patterns with Gut Microbial Enterotypes", Science, Oct. 7, 2011, 5 pgs., vol. 334.

Monica P. Mcnamara et al., "Early-life effects of juvenile Western diet and exercise on adult gut microbiome composition in mice", Journal of Experimental Biology, 2021, pp. 1-11, vol. 224.

International Search Report for PCT/KR2022/001667 dated, May 12, 2022 (PCT/ISA/210).

* cited by examiner

*Primary Examiner* — Melissa S Mercier
(74) *Attorney, Agent, or Firm* — Sughrue Mion, PLLC

(57) ABSTRACT

The present disclosure relates to a composition for preventing, alleviating or treating sleep disorder, containing, as an active ingredient, *Prevotella histicola*, a culture product thereof, a crushed product thereof, an extract thereof or a fermented product thereof; or extracellular vesicles derived from *Prevotella histicola*. The *Prevotella histicola* or extracellular vesicles contained in the composition of the present disclosure can be used as a safe drug for preventing and treating sleep disorder by increasing total sleep time, non-REM (NREM) sleep time and REM sleep time and decreasing sleep latency and waking time.

14 Claims, 8 Drawing Sheets

FIG. 1

| Experimental procedure | Period (days) |
|---|---|
| Acquisition/adaptation of white rats | 7 days |
| Administration of distilled water | 5 days |
| Surgery/recovery | 10 days |
| Administration of medium or physiological saline: baseline sleep measurement | 1-2 days |
| Start of administration of live cells or EVs: sleep measurement | 6-7 days |
| Stopping of administration of live cells: sleep measurement | 3 days |

FIG. 2

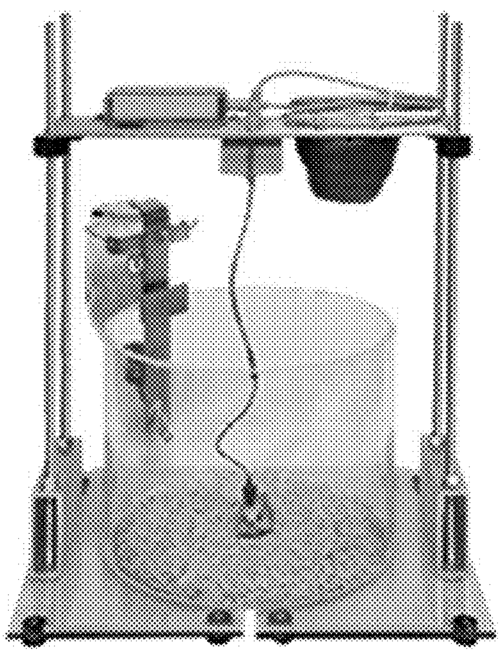

Test_D1: Day 1 after administration of microorganisms
Test_D4: Day 4 after administration of microorganisms
Test_D7: Day 7 after administration of microorganisms Test_D1: Day 1 after administration of microorganisms
Test_D4: Day 4 after administration of microorganisms
Test_D7: Day 7 after administration of microorganisms Test_D1: Day 1 after administration of microorganisms
Test_D4: Day 4 after administration of microorganisms
Test_D7: Day 7 after administration of microorganisms Test_D1: Day 1 after administration of microorganisms, Test_D4: Day 4 after administration of microorganisms, Test_D7: Day 7 after administration of microorganisms, R_D1: Day 1 after stopping of administration, R_D2: Day 2 after stopping of administration, R_D3: Day 3 after stopping of administration Test_D1: Day 1 after administration of microorganisms,
Test_D4: Day 4 after administration of microorganisms,
Test_D7: Day 7 after administration of microorganisms,
R_D1: Day 1 after stopping of administration,
R_D2: Day 2 after stopping of administration,
R_D3: Day 3 after stopping of administration Baseline: Value for 1-2 day(s) before administration of EVs (average value in case of 2 days)
Test_D1: Day 1 after administration of EVs, Test_D3: Day 3 after administration of EVs,
Test_D6: Day 6 after administration of EVs

COMPOSITION FOR PREVENTING, ALLEVIATING OR TREATING SLEEP DISORDERS, CONTAINING, AS ACTIVE INGREDIENT, GUT MICROBIOTA OR EXTRACELLULAR VESICLES DERIVED THEREFROM

CROSS REFERENCE TO RELATED APPLICATIONS

This application is a National Stage of International Application No. PCT/KR2022/001667 filed on Jan. 28, 2022, claiming priority based on Korean Patent Application No. 10-2021-0015295 filed on Feb. 3, 2021, Korean Patent Application No. 10-2021-0087932 filed on Jul. 5, 2021, and Korean Patent Application No. 10-2022-0011607 filed on Jan. 26, 2022.

TECHNICAL FIELD

The present disclosure relates to a pharmaceutical composition for preventing or treating sleep disorder and/or a food composition for preventing or alleviating sleep disorder.

BACKGROUND ART

The size of the insomnia treatment market in the US is about 2 trillion won and has recently shown a growth rate of 20% or more every year. The representative sleep disorder drug in the US is a product called Stilnox and it represents about 50% of the market share also in Korea. In general, sleeping pills are effective when used for a short period of time, but long-term use of 4 weeks or longer has problems of dependence and side effects. Especially, the elderly people with a high prevalence of insomnia need to be careful of the side effects when taking the pills. Therefore, interest in natural sleep aids that can replace sleeping pills is increasing gradually and the market size is expanding. Currently, there are more than 10 natural sleep aids that are most commonly used in the US and European countries, but reports showing the effectiveness of these sleep aids for treatment of insomnia through scientific studies are very limited. According to a consumer report in the US, 64% of people who used sleeping pills and 20% of those who used sleep aids experienced a sleep-enhancing effect, indicating that the actual usefulness of sleep aids is very low. In Korea, there is almost no domestic natural sleep aid product approved by the Ministry of Food and Drug Safety as a health functional food for sleep promotion and improvement, and researches on related functional raw materials are also limited. It is predicted that the need to solve insomnia while reducing medical expenses will increase with the increase in the elderly population in the future. Therefore, the discovery of a safe and inexpensive natural substance for enhancing sleep is required.

Gut microbiota (gut flora or microbiome) refers to microorganisms, including bacteria, archaea, fungi, etc., that live in the human digestive tracts. According to various studies and statistical data, it was found out that the gut microbiota consists mainly of three enterotypes: *Prevotella, Bacteroides* and *Ruminococcus*.

Among these, the microorganisms in the genus *Prevotella* are known to be mainly related to carbohydrates and monosaccharides and the microorganisms in the genus *Bacteroides* are known to be related to proteins, amino acids and saturated fats. One of the enterotypes may predominate depending on diet, and change in the diet causes corresponding changes in the number of species (Wu et al, "Linking Long-Term Dietary Patterns with Gut Microbial Enterotypes". Science, 2011). According to a research in 2021, it was reported that the diet and exercise in childhood can significantly affect the overall composition and diversity of microorganisms in adulthood (Monica P. McNamara et al, "Early-life effects of juvenile Western diet and exercise on adult gut microbiome composition in mice", *The Journal of Experimental Biology,* 2021).

Therefore, researches to confirm the relationship between the composition and diversity of the gut microbiota changed by the diet and lifestyles with the occurrence or progression of diseases are increasing.

However, the researches on the correlation between the gut microbiota and the sleep pattern in mammals including human or the researches on natural sleep aids using the gut microbiota are still insufficient. If a sleep aid utilizing the gut microbiota existing already in the human body is developed, it will be possible to provide safer sleep without tolerance while exhibiting a long-lasting effect.

The matters described above in the background art section is only for improving the understanding of the background of the present disclosure, and should not be taken as an admission that they correspond to the prior art already known to those having ordinary knowledge in the art.

DISCLOSURE

Technical Problem

The inventors of the present disclosure have made consistent efforts to develop a safer sleep aid derived from a natural product. As a result, they have identified that *Prevotella histicola*, which is one of the human gut microbiota, or a culture thereof has the effect of increasing sleep time and reducing sleep latency and waking time, and have completed the present disclosure.

The present disclosure is directed to providing a composition for preventing, alleviating or treating sleep disorder, which contains *Prevotella histicola*, a culture product thereof, a crushed product thereof, an extract thereof or a fermented product thereof as an active ingredient.

The present disclosure is also directed to providing a composition for preventing, alleviating or treating sleep disorder, which contains extracellular vesicles derived from *Prevotella histicola* as an active ingredient.

The present disclosure is also directed to providing a method for preventing, alleviating or treating sleep disorder, which includes a step of administering a composition containing *Prevotella histicola*, a culture product thereof, a crushed product thereof, an extract thereof or a fermented product thereof to a subject.

The present disclosure is also directed to providing a method for preventing, alleviating or treating sleep disorder, which includes a step of administering a composition containing extracellular vesicles derived from *Prevotella histicola* to a subject.

The present disclosure is also directed to providing a therapeutic use of *Prevotella histicola*, a culture product thereof, a crushed product thereof, an extract thereof or a fermented product thereof.

The present disclosure is also directed to providing a therapeutic use of extracellular vesicles derived from *Prevotella histicola*.

The present disclosure is also directed to providing a method for preparing a composition for preventing, alleviating or treating sleep disorder, which includes:

(a) a step of preparing a *Prevotella histicola* strain; and (b) a step of culturing the strain in a culture medium.

The present disclosure is also directed to providing a method for preparing a composition for preventing, alleviating or treating sleep disorder, which includes a step of preparing extracellular vesicles derived from a *Prevotella histicola* strain.

Other purposes and advantages of the present disclosure will become more apparent from the following detailed description, claims and drawings.

Technical Solution

In an aspect, the present disclosure provides a composition for preventing, alleviating or treating sleep disorder, which contains *Prevotella histicola*, a culture product thereof, a crushed product thereof, an extract thereof or a fermented product thereof as an active ingredient.

In another aspect, the present disclosure provides a composition for preventing, alleviating or treating sleep disorder, which contains extracellular vesicles derived from *Prevotella histicola* as an active ingredient.

In the present specification, the term "*Prevotella histicola*" or "*Prevotella histicola* strain" refers to a strain in the genus *Prevotella*, which is an anaerobic, non-motile gram-negative bacilli living symbiotically in the human oral cavity or gastrointestinal tract. Specifically, the *Prevotella histicola* or *Prevotella histicola* strain is *Prevotella histicola* with an accession number selected from a group consisting of KCTC 15171, CCUG 55407, DSM 19854, JCM 15637, CCUG 60372, KCCM13103P, KCCM13104P and KCCM13105P.

In the accession numbers, KCTC stands for the Korean Collection for Type Cultures, CCUG stands for the Culture Collection University of Gothenburg, DSM stands for the DSMZ-German Collection of Microorganisms and Cell Cultures GmbH, JCM stands for the Japan Collection of Microorganisms, and KCCM stands for the Korean Culture Center of Microorganisms.

It is known that the *Prevotella histicola* with the accession number KCTC 15171 is the same as the strains of CCUG 55407, DSM 19854 and JCM 15637. More specifically, the *Prevotella histicola* is selected from a group consisting of KCCM13103P (*Prevotella histicola* KCOM 3796), KCCM13104P (*Prevotella histicola* KCOM 4081) and KCCM13105P (*Prevotella histicola* KCOM 4227) deposited in the Korean Culture Center of Microorganisms on Jan. 11, 2022.

The *Prevotella histicola* contained in the composition according to the present disclosure may exist as live or dead cells and may also be in a dried or lyophilized form. The types of lactic acid bacteria suitable for inclusion in the composition and the formulation methods thereof are well known those skilled in the art. For example, the *Prevotella histicola* may be a culture obtained by culturing in a known liquid or solid medium, a fermentation product obtained by culturing the strain with additional components, an extract obtained by extracting the strain with an organic solvent, a lysate obtained by lysing, crushing or homogenizing the strain, etc., although not being limited thereto.

In a specific exemplary embodiment, the composition may be a composition containing a *Prevotella histicola* strain existing as live or dead cells.

In another specific exemplary embodiment, the composition may be a composition containing a culture, lysate, extract or fermentation product of a *Prevotella histicola* strain.

In another specific exemplary embodiment, the composition may be a composition containing extracellular vesicles derived from *Prevotella histicola*, a culture product thereof, a crushed product thereof, an extract thereof or a fermented product thereof.

Extracellular vesicles (EVs) enable the exchange of substances (proteins, lipids and materials) between cells and function as a physiological/pathological signal transduction medium. The extracellular vesicles are largely classified into exosomes and microvesicles. The exosomes vary in size depending on their biological origin. They are intraluminal vesicles formed through the inward budding of the endosomal membrane during the maturation of multivesicular endosomes. They are secreted when the multivesicular endosomes are bound to the cell surface. The microvesicles are vesicles with a size of 50-1000 nm, which bud out of the plasma membrane and are released out of cells. Each cell produces different extracellular vesicles depending on physiological conditions and secrete extracellular vesicles having specific lipid/protein/nucleic acid compositions (Jaewook Lee (2019). A light on the cell biology of the extracellular vesicles. BRIC View 2019-R03).

In the present specification, the term "extracellular vesicles" encompasses the meanings of the exosomes and the microvesicles.

The exosomes or extracellular vesicles have various diameters within a range of about 1-1,000 nm. The *Prevotella histicola*-derived exosomes may have a diameter of specifically 10-800 nm, most specifically 10-600 nm.

The exosomes or extracellular vesicles contained in the composition of the present disclosure are included in large quantities in a culture of *Prevotella histicola* (e.g., a culture supernatant).

Since the exosomes or extracellular vesicles are included in large quantities in a culture of *Prevotella histicola* (e.g., culture supernatant), the exosomes or extracellular vesicles isolated and purified therefrom may be used as a therapeutic agent or a culture, lysate, extract or fermentation product including the exosomes or extracellular vesicle in large quantities may be used as a therapeutic agent.

In the present specification, the term "isolation" or "extraction" includes not only a process of selectively obtaining a desired substance (e.g., exosomes) in a biological sample (e.g., a culture of *Prevotella histicola*) (positive isolation) but also a process of selectively removing impurities other than the desired substance (negative isolation). Accordingly, the term "isolation" can be used synonymously with "obtainment", "extraction" and "purification". For the isolation of the exosomes or extracellular vesicles, all methods commonly used in the art may be used without limitation. For example, commercially available exosome isolation kits (e.g., EXO-BB, ExoQuick®-ULTRA, ExoQuick®-TC, Capturem™ exosome isolation kit, total exosome isolation kit, ExoTrap™ exosome isolation spin column kit, Exo2D™, etc.), separation according to the difference in the specific gravity of components in a solution (e.g., centrifugation), separation according to size (e.g., ultrafiltration or vacuum filtration) or separation based on affinity for a particular substrate (e.g., affinity chromatography) may be included. However, any method commonly used in the art for separation of a target substance from a nonhomogeneous sample based on its intrinsic properties may be used without limitation.

In a specific exemplary embodiment of the present disclosure, the culture, lysate, extract or fermentation product of *Prevotella histicola* may include the intracellular vesicles, intraluminal vesicles (ILVs), endosomes and/or multivesicular endosomes (MVEs) of *Prevotella histicola.*

The intracellular vesicles may be secreted as exosomes through binding with the plasma membrane of *Prevotella histicola.*

In a specific exemplary embodiment of the present disclosure, the culture, lysate, extract or fermentation product of *Prevotella histicola* may include the extracellular vesicles (EVs) of *Prevotella histicola*, which include microvesicles and/or exosomes.

In a specific exemplary embodiment of the present disclosure, the sleep disorder is one or more selected from a group consisting of insomnia, breathing-related sleep disorder and circadian rhythm sleep disorder.

In the present specification, the term "insomnia" refers to a state of trouble with sleep lasting for days, which impedes daytime activities.

The insomnia is largely classified into three types: sleep onset insomnia with difficulty falling asleep, sleep maintenance insomnia with frequent waking during sleep and difficulty falling back to sleep, and sleep terminal insomnia with waking up early in the morning and not being able to sleep.

In the present specification, the term "breathing-related sleep disorder" refers to a case in which drowsiness or insomnia is caused by a breathing disorder during sleep. Breathing disorders make it difficult to breathe regularly or stop breathing for a while during sleep, resulting in waking. The main symptom is excessive drowsiness, which occurs because you cannot get a good night's sleep because you wake up frequently to breath normally during the night sleep.

There are three main types of breathing disorder occurring in breathing-related sleep disorder. The first is obstructive sleep apnea syndrome, in which the airway is blocked during sleep and apnea or hypnea occurs repeatedly. It is the most common type. The second is central sleep apnea syndrome, which refers to a case in which apnea occurs during sleep due to neurological or heart disease, although there is no obstruction of the airway. Finally, central alveolar hypoventilation syndrome is a phenomenon in which arterial oxygen level is decreased due to impaired respiratory control.

In the present specification, the term "circadian rhythm sleep disorder" refers to recurrent drowsiness or insomnia due to change in the sleep-wake cycle. In other words, excessive drowsiness or insomnia is repeated and sustained due to the mismatch of the sleep-wake cycle required by the environment (e.g., night shift, overseas trip, etc.) and the individual's circadian sleep-wake cycle.

The circadian rhythm sleep disorder is divided into four types. The first type is a delayed sleep phase type, in which the individual's sleep-wake cycle is delayed as compared to what is socially required. The second type is an advanced sleep phase type, which refers to a sleep cycle of falling asleep early in the evening and waking up at the early dawn. It is common in the elderly. The third type is a jet lag type, in which the sleep-wake cycle required in the new time zone due to overseas trip and the individual's sleep-wake cycle do not match. The fourth type is a shift work type, in which the sleep-wake cycle required due to shift work and the individual's sleep-wake cycle do not match.

In a specific exemplary embodiment of the present disclosure, the prevention, alleviation or treatment of sleep disorder may be achieved by increase of total sleep time.

In an example of the present disclosure, a *Prevotella histicola* administration group showed increased total sleep time (24 hours) as compared to *Prevotella stercorea* as a control group (FIG. 3).

In a specific exemplary embodiment of the present disclosure, the prevention, alleviation or treatment of sleep disorder may be achieved by increase of non-REM (NREM) sleep time.

In an example of the present disclosure, a *Prevotella histicola* administration group showed increased non-REM sleep time as compared to *Prevotella stercorea* as a control group (FIG. 4).

In a specific exemplary embodiment of the present disclosure, the prevention, alleviation or treatment of sleep disorder may be achieved by increase of REM sleep time.

In an example of the present disclosure, a *Prevotella histicola* administration group showed increased REM sleep time as compared to *Prevotella stercorea* as a control group (FIG. 5).

In a specific exemplary embodiment of the present disclosure, the prevention, alleviation or treatment of sleep disorder may be achieved by decrease of sleep latency.

In an example of the present disclosure, a *Prevotella histicola* administration group showed decreased sleep latency in general as compared to *Prevotella stercorea* as a control group (FIG. 6).

In a specific exemplary embodiment of the present disclosure, the prevention, alleviation or treatment of sleep disorder may be achieved by decrease of total waking time.

In an example of the present disclosure, a *Prevotella histicola* administration group showed decreased waking time in general as compared to *Prevotella stercorea* as a control group (FIG. 7).

In an example of the present disclosure, *Prevotella histicola* strain-derived extracellular vesicles showed increased total sleep time and decreased total waking time (FIG. 9).

In an example of the present disclosure, *Prevotella histicola* strain-derived extracellular vesicles showed increased non-REM sleep time (FIG. 10).

In a specific exemplary embodiment of the present disclosure, the composition is a pharmaceutical composition.

In another aspect, the present disclosure provides a method for preventing, alleviating or treating sleep disorder, which includes a step of administering a therapeutically effective amount of *Prevotella histicola*, a culture product thereof, a crushed product thereof, an extract thereof or a fermented product thereof; or extracellular vesicles derived from *Prevotella histicola*, a culture product thereof, a crushed product thereof, an extract thereof or a fermented product thereof to a subject in need thereof.

In another aspect, the present disclosure provides a therapeutic use of *Prevotella histicola*, a culture product thereof, a crushed product thereof, an extract thereof or a fermented product thereof.

In another aspect, the present disclosure provides a therapeutic use of extracellular vesicles derived from *Prevotella histicola*, a culture product thereof, a crushed product thereof, an extract thereof or a fermented product thereof.

In a specific exemplary embodiment of the present disclosure, the therapeutic use is a therapeutic use for sleep disorder.

As used herein, the "subject" refers to a mammal that is the subject of treatment, observation or experimentation and may specifically be human or an animal requiring the prevention, alleviation and/or treatment of sleep disorder.

The pharmaceutical composition according to the present disclosure may be administered orally or parenterally.

The parenteral administration may be made, for example, by intravenous injection, transdermal administration, subcutaneous injection, intramuscular injection, intravitreal injection, eye drop administration, intracerebroventricular injection, intrathecal injection, intraamniotic injection, intraarterial injection, intraarticular injection, intracardiac injection, intracavernous injection, intracerebral injection, intracisternal injection, intracoronary injection, intracranial injection, intradural injection, epidural injection, intrahippocampal injection, intranasal injection, intraosseous injection, intraperitoneal injection, intrapleural injection, intraspinal injection, intrathoracic injection, intrathymic injection, intrauterine injection, intravaginal injection, intraventricular injection, intravesical injection, subconjunctival injection, intratumoral injection, topical injection, etc.

The pharmaceutical composition of the present disclosure may contain a pharmaceutically acceptable carrier. In the present specification, the term "pharmaceutically acceptable carrier" refers to a carrier or a diluent that is not significantly irritant to organisms and does not interfere with the biological activity and properties of the administered ingredient. In the present specification, the pharmaceutically acceptable carrier may be one or more of saline, sterile water, Ringer's solution, buffered saline, dextrose solution, maltodextrin solution, glycerol and ethanol. If necessary, other common additives such as an antioxidant, a buffer, a bacteriostat, etc. may be added to formulate an injection suitable for injection into tissues or organs. In addition, the composition may be formulated into an isotonic sterile solution or a dry preparation (particularly a freeze-dried preparation) that can be prepared into an injectable solution by adding sterile water or physiological saline as the case may be. In addition, a target organ-specific antibody or other ligands may be bound to the carrier for specific action on the target organ. Suitable formulations known in the art may be referred to in the literature (Remington's Pharmaceutical Science, Mack Publishing Company, Easton PA).

In addition, the composition of the present disclosure may further contain a filler, an excipient, a disintegrant, a binder, a glidant, etc. In addition, the composition of the present disclosure may be formulated by the methods known in the art so as to provide rapid, sustained or delayed release of the active ingredient after administration to a mammal.

In the present specification, the "administration" means introducing the composition of the present disclosure to a subject by any appropriate method, and the administration of the composition of the present disclosure may be made through various oral or parenteral routes that can reach the target tissue.

For example, the composition of the present disclosure may be administered by intramuscular, intravenous or intraperitoneal injection in clinical administration.

Specifically, the composition can be formulated into pharmacologically compatible buffers such as Hank's solution, Ringer solution or physiological saline buffer for injection. For transmucosal administration, an impermeable agent suitable for the barrier is used in the formulation. Such impermeable agents are generally known in the art.

Formulations for parenteral administration include a sterilized aqueous solution, a nonaqueous solution, a suspension, an emulsion, etc. In the nonaqueous solution or suspension, propylene glycol, polyethylene glycol, a vegetable oil such as olive oil, an injectable ester such as ethyl oleate, etc. may be used.

In the present specification, the "effective amount" means an amount required to delay or completely stop the onset or progression of a specific disease to be treated, and the effective amount of *Prevotella histicola* contained in the pharmaceutical composition of the present disclosure means an amount required to achieve the effect of preventing, alleviating or treating sleep disorder. Therefore, the effective amount may be controlled depending on various factors including the type of a disease, the severity of the disease, the type and amount of other ingredients contained in the composition, the age, body weight, general health condition, sex and diet of a patient, administration time, administration route, treatment period, and drugs used tougher. It is obvious to those skilled in the art that an appropriate total daily dosage can be determined by a physician within the scope of medical judgment.

For the purpose of the present disclosure, the specific therapeutically effective amount for a particular patient depends on factors such as the type and extent of response to be achieved, use of other agents, the age, body weight, general health condition, sex and diet of a patient, administration time, administration route, excretion rate of the composition, treatment period and drugs use together or concurrently with the composition and other similar factors well known in the medical field.

In the present specification, the "treatment" refers to an approach for obtaining beneficial or desirable clinical results. For the purpose of the present disclosure, the beneficial or desirable clinical results include, but are not limited to, alleviation of symptoms, reduction of disease extent, stabilization of disease state (i.e., prevention of worsening), delay or slowing of disease progression, (partial or total) improvement, transient palliation or alleviation disease state, and possibility of detection. In addition, the "treatment" can also mean increasing survival rate compared to that expected for the absence of treatment. The "treatment" refers to both therapeutic and prophylactic or preventive measures. The treatment includes the treatment of predicted disorders and those that have occurred already. The "alleviation" or "mitigation" of a disease means reduction of the extent of disease state and/or undesirable clinical symptoms and/or slowing or prolonging of the progression of the disease compared to those expected for the absence of treatment.

In a specific exemplary embodiment of the present disclosure, the composition of the present disclosure is a food composition.

*Prevotella histicola*, a culture product thereof, a crushed product thereof, an extract thereof or a fermented product thereof; or extracellular vesicles derived from *Prevotella histicola*, a culture product thereof, a crushed product thereof, an extract thereof or a fermented product thereof contained in the food composition of the present disclosure are the same as described above.

When the composition of the present disclosure is used as a food composition, the food composition may be in the form of a health functional food, a condiment, a beverage, a bar, etc. In addition, the food composition containing the strain as an active ingredient may be in the form of a beverage such as fermented milk. Accordingly, the present disclosure provides a lactic acid bacteria starter for fermentation, which contains *Prevotella histicola* or a culture thereof.

The food composition of the present disclosure may be prepared using, in addition to the active ingredient, a sitologically appropriate and physiologically acceptable adjuvant. As the adjuvant, an excipient, a disintegrant, a sweetener, a binder, a coating agent, a swelling agent, a lubricant, a glidant, a flavorant, etc. may be used.

The food composition may specifically be formulated by using one or more sitologically acceptable carrier in addition to the above-described active ingredient.

For example, for formulation into a tablet or a capsule, the active ingredient may be combined with an oral, nontoxic, pharmaceutically acceptable, inert carrier such as ethanol, glycerol, water, etc. In addition, if desired or necessary, a suitable binder, lubricant, disintegrant or colorant may be included in the mixture. Suitable binders include, but are not limited to, starch, gelatin, natural sugar such as glucose or beta-lactose, corn sweetener, natural or synthetic gum such as acacia, tragacanth or sodium oleate sodium stearate, magnesium stearate, sodium benzoate, sodium acetate, sodium chloride, etc. The disintegrant includes, but is not limited to, starch, methylcellulose, agar, bentonite, xanthan gum, etc. When the composition is formulated as a liquid solution, one or more of saline, sterile water, Ringer's solution, buffered saline, albumin injection solution, dextrose solution, maltodextrin solution, glycerol and ethanol may be used as a pharmaceutically acceptable carrier which is sterile and biocompatible. If necessary, other common additives such as an antioxidant, a buffer, a bacteriostat, etc. may be added. In addition, a diluent, a dispersant, a surfactant, a binder or a lubricant may be added additionally to formulate an injectable formulation such as an aqueous solution, a suspension, an emulsion, etc., a pill, a capsule, a granule or a tablet.

The food composition according to the present disclosure can be added to various foods. The foods to which the composition of the present disclosure can be added include, for example, beverages, vitamin complexes, health supplements, etc.

The food composition of the present disclosure may contain ingredients commonly added for preparation of foods including, for example, proteins, carbohydrates, fats, nutrients, condiments and flavorants. Examples of the carbohydrates include common sugars such as monosaccharides, e.g., glucose, fructose, etc.; disaccharides, e.g., maltose, sucrose, oligosaccharides, etc.; and polysaccharides, e.g., dextrin, cyclodextrin, etc. and sugar alcohols such as xylitol, sorbitol, erythritol, etc. As the flavorant, natural flavorants [thaumatin and *stevia* extract (e.g., rebaudioside A, glycyrrhizin, etc.)] and synthetic flavorants (saccharin, aspartame, etc.) may be used. For example, when the food composition of the present disclosure is prepared into drinks or beverages, citric acid, high-fructose corn syrup, sugar, glucose, acetic acid, malic acid, fruit juice, plant extract, etc. may be further included.

In another aspect, the present disclosure provides a feed additive or a feed containing *Prevotella histicola*, a culture product thereof, a crushed product thereof, an extract thereof or a fermented product thereof; or extracellular vesicles derived from *Prevotella histicola*, a culture product thereof, a crushed product thereof, an extract thereof or a fermented product thereof as an active ingredient.

When used as a feed additive, the composition may be prepared into a 20-90% concentrate, a powder or a granule. The feed additive may further contain one or more of an organic acid such as citric acid, fumaric acid, adipic acid, lactic acid, malic acid, etc., a phosphate such as sodium phosphate, potassium phosphate, acidic pyrophosphate, polyphosphate, etc., or a natural antioxidant such as polyphenol, catechin, alpha-tocopherol, rosemary extract, vitamin C, green tea extract, licorice extract, chitosan, tannic acid, Pythic acid, etc. When used as a feed, the composition may be formulated into a common feed form and may contain common feed ingredients.

The feed additive and feed may include grains, e.g., milled or crushed wheat, oats, barley, corn and rice; vegetable protein feeds, e.g., rape-, soybean- and sunflower-based feeds; animal protein feeds, e.g., blood meal, meat meal, bone meal and fish meal; sugars; and dairy products, e.g., powdered milk and whey powder, and may further include nutritional supplements, digestion and absorption enhancers, growth promoters, etc.

The feed additive may be administered to an animal either alone or in combination with other feed additives in an edible carrier. In addition, the feed additive can be easily administered to animals as a top dressing, mixed directly with an animal feed or easily administered as a separate oral formulation. When the feed additive is administered separately from an animal feed, it can be combined with a sitologically acceptable and edible carrier well known in the art for preparation into a formulation for immediate or sustained release. The edible carrier may be solid or liquid, e.g., cornstarch, lactose, sucrose, soybean flakes, peanut oil, olive oil, sesame oil and propylene glycol. When a solid carrier is used, the feed additive may be a tablet, a capsule, a powder, a troche, a sugar-coated tablet or a microdispersible top dressing. When a liquid carrier is used, the feed additive may be in the form of a soft gelatin capsule, a syrup, a suspension, an emulsion or a solution.

In addition, the feed additive and feed may contain an adjuvant, e.g., a preservative, a stabilizer, a wetting agent, an emulsifier, a solution accelerator, etc. The feed additive may be added to an animal feed through steeping, spraying or mixing.

The feed or feed additive of the present disclosure may be applied to a number of feeds for animals including mammals, poultry and fish.

The mammal may be not only pig, cow, sheep, goat and laboratory rodents but also pets (e.g., dog or cat), the poultry may be chicken, turkey, dog, goose, pheasant, quail, etc., and the fish may be trout, etc., although not being limited thereto.

The feed or feed additive of the present disclosure may be applied to animal diets for the growth and immunity enhancement of animals.

The amount of the *Prevotella histicola* strain contained in the composition according to the present disclosure may be about $10^6$-$10^{12}$ CFU/mL, e.g., $10^7$-$10^{11}$ CFU/mL or $10^8$-$10^{11}$ CFU/mL, for a single dose. Specifically, the strain may be administered as live cells and may be killed or attenuated before ingestion. In addition, when the composition is prepared using a culture supernatant, etc., a sterilization process through heat treatment may be performed additionally. The amount of the strain required to achieve the minimum effect and the amount of daily intake may vary depending on the physical or health condition of the consumer, but may generally be about $10^8$-$10^{12}$ CFU/mL, e.g., $10^7$-$10^{11}$ CFU/mL or $10^8$-$10^{11}$ CFU/mL.

The amount of the *Prevotella histicola* strain-derived extracellular vesicles contained in the composition according to the present disclosure may be the amount of the extracellular vesicles isolated from about $10^6$-$10^{12}$ CFU/mL, e.g., $10^7$-$10^{11}$ CFU/mL or $10^8$-$10^{11}$ CFU/mL, for a single dose.

In another aspect, the present disclosure provides a method for preparing a composition for preventing, alleviating or treating sleep disorder, which includes:

(a) a step of preparing a *Prevotella histicola* strain; and (b) a step of culturing the strain in a culture medium.

In a specific exemplary embodiment of the present disclosure, the preparation method may further include: (c) a step of isolating extracellular vesicles from the culture.

In another aspect, the present disclosure provides a method for preparing a composition for preventing, alleviating or treating sleep disorder, which includes a step of preparing extracellular vesicles derived from a *Prevotella histicola* strain.

Advantageous Effects

The features and advantages of the present disclosure may be summarized as follows:

(i) The present disclosure provides a composition for preventing, alleviating or treating sleep disorder, which contains *Prevotella histicola*, a culture product thereof, a crushed product thereof, an extract thereof or a fermented product thereof; or extracellular vesicles derived from *Prevotella histicola* as an active ingredient.

(ii) The *Prevotella histicola* or extracellular vesicles contained in the composition of the present disclosure can be used as a safe drug for preventing and treating sleep disorder by increasing total sleep time, non-REM (NREM) sleep time and REM sleep time and decreasing sleep latency and waking time.

BRIEF DESCRIPTION OF DRAWINGS

FIG. 1 schematically shows the entire experimental procedure and period.

FIG. 2 shows the image of a sleep electroencephalography system.

BEST MODE

Figure 3:
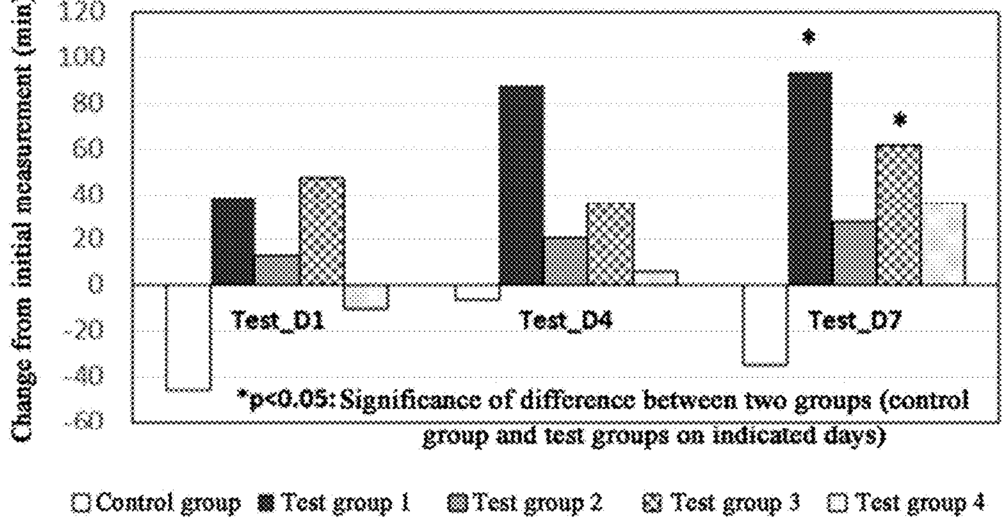
FIG. 3 shows a result of comparing initially measured sleep time (recorded for 24 hours) and changed sleep time (recorded for 24 hours) in sleep electroencephalography.

Hereinafter, the present disclosure is described in more detail through examples. These examples are only for describing the present disclosure more specifically, and it will be obvious to those having ordinary knowledge in the art that the scope of the present disclosure is not limited by the examples.

EXAMPLE

Research Materials and Methods

1. Experimental Animals 7-week-old Sprague-Dawley white rats were used for the experiment. All animals were adapted to a light/dark cycle of 09:00 to 21:00 for a week at constant temperature (20-21° C.) with free access to water and feed.

2. Design of Animal Experiments Using Live Strains

Animal experiments using live strains were conducted for a control group (n=5) and four test groups, i.e., test group 1 (n=5), test group 2 (n=5), test group 3 (n=4) and test group 4 (n=6). The entire experimental procedure and period are shown in FIG. 1. For the control group, a *Prevotella stercorea* (the second most abundant microorganism of the genus *Prevotella* found in the human body) sample was orally administered. For the test group 1, the representative *Prevotella histicola* strain (KCTC 15171; CCUG 55407; DSM 19854; JCM 15637) samples were orally administered. For the test group 2, another *Prevotella histicola* strain (CCUG 60372) sample was orally administered. For the test group 3 and the test group 4, *Prevotella histicola* (test group 3: KCCM13103P, test group 4: KCCM13105P) samples collected from the oral cavities of Koreans were orally administered. For adaptation to oral administration, 1 mL of distilled water was orally administered at the same hour (between 08:00 and 09:00) every day from 5 days before the start of sleep measurement. For the control group, the test group 1 and the test group 2, 1 mL of a medium was orally administered between 08:00 and 09:00 for two days and baseline sleep measurement was conducted for two days before the administration of the microorganisms. Then, live cell samples cultured in media were administered. For the test group 3 and the test group 4, distilled water was orally administered between 08:00 and 09:00 and baseline sleep measurement was conducted for 1-2 days before the administration of freeze-dried live cell samples diluted in distilled water without media. The microorganisms used for each test group were subjected to genetic analysis (16S rDNA sequencing) for identification and the number of live cells in the sample administered every day was $1\times10^{10}$ CFU.

3. Design of Animal Experiments for Administration of Extracellular Vesicles (EVs) of Strains Animal experiments using EVs were two test groups with n=4. For the test group 5, the EV sample of the representative *Prevotella histicola* strains (KCTC 15171; CCUG 55407; DSM 19854; JCM 15637) was orally administered. For the test group 6, the EV sample of *Prevotella histicola* (KCCM13105P) collected from the oral cavities of Koreans was orally administered. For adaptation to oral administration, 1 mL of distilled water was orally administered at the same hour (between 08:00 and 09:00) every day from 5 days before the start of sleep measurement. The amount of the EV samples orally administered every day was 4.56 mg (the amount collected from $1\times10^{9}$ CFU of live cells) for the test group 5 and 2 mg for the test group 6.

4. Sleep Electroencephalographic Measurement

The sleep state of the white rats was analyzed by electroencephalography (EEG 2, channel) and electromyography (EMG, 1 channel) (8239 Headmount, Pinnacle Technology Inc.). Surgery was performed to implant a device for testing into the skull, and the method is as follows. After inducing deep anesthesia (isoflurane anesthesia) and cutting the white rat's hair on the head using a cutter, the head was fixed on a stereotaxic device and the scalp and the subcutaneous connective tissue were incised together using a scalpel to expose the skull. After drilling holes on four parts of the skull using a dental drill, EEG electrodes were inserted for EEG measurement and EMG electrodes were inserted into two parts of the neck muscle for EMG, which were then fixed using a non-absorbable thread and dental acryl. After the incision was sutured and disinfected, antibiotics were administered intraperitoneally for 3 days to prevent surgical inflammation. Sleep electroencephalography measurement was started after a recovery period of at least 10 days while washing the wound site after the surgery. EEG and EMG recordings were taken continuously for 24 hours starting from 9 am. For sleep stage analysis, the white rat was placed in a cage and connected to a preamplifier. A 3-channel EEG/EMG system (Sirenia Sleep Pro, Pinnacle Technology, Oregon ST, USA) was used for sleep recording (FIG. 2). The sleep stages were analyzed by dividing them into wake, non-REM (non-rapid eye movement, deep sleep) sleep and REM (rapid eye movement, light sleep) sleep according to the amplitude values of the EEG and EMG waveforms. The brain waves were acquired under the condition of sampling rate 200 Hz and preamplification gain 10, and the channel acquisition conditions were set to gain 1 and filter Hz 25 for EEG, and gain 1, filter Hz 100 for EMG.

Results

1. Result of Animal Experiments Using Live Strains

The sleep electroencephalography results were obtained for all the experimental white rats. The baseline sleep measurement values were measured for 1-2 days (the average value was used in case of 2 days), and the sleep measurements were recorded on days 1, 4 and 7 after the administration of the microorganisms (for all the groups) and on days 1-3 after the stopping of the administration of the microorganisms (only for the control group, test group 1 and test group 4). For the control group and the test groups, the change in the sleep measurement values from the baseline sleep measurement values (sleep measurement value−baseline sleep measurement value) was compared. The Mann-Whitney U test, which is a non-parametric statistical method, was used for statistical verification, and $p<0.05$ was considered to be significant in the two-tailed test.

FIG. 3 shows a result of comparing initially measured sleep time (recorded for 24 hours) and changed sleep time (recorded for 24 hours) in sleep electroencephalography. In general, the test groups showed a gradual increase in sleep time after the administration of the microorganisms as compared to the baseline sleep measurement values, whereas the control group showed little change or slight decrease in sleep time. In particular, the test group 1 and the test group 3 showed sleep time increased by 1 hour or longer on day 7 after the administration of the microorganisms as compared to before the administration, as compared to the control group ($p<0.05$). The test group 2 and the test group 4 also showed increase in sleep time on day 7 after the administration of the microorganisms as compared to before the administration, although the increase was not spastically significant.

Figure 4:
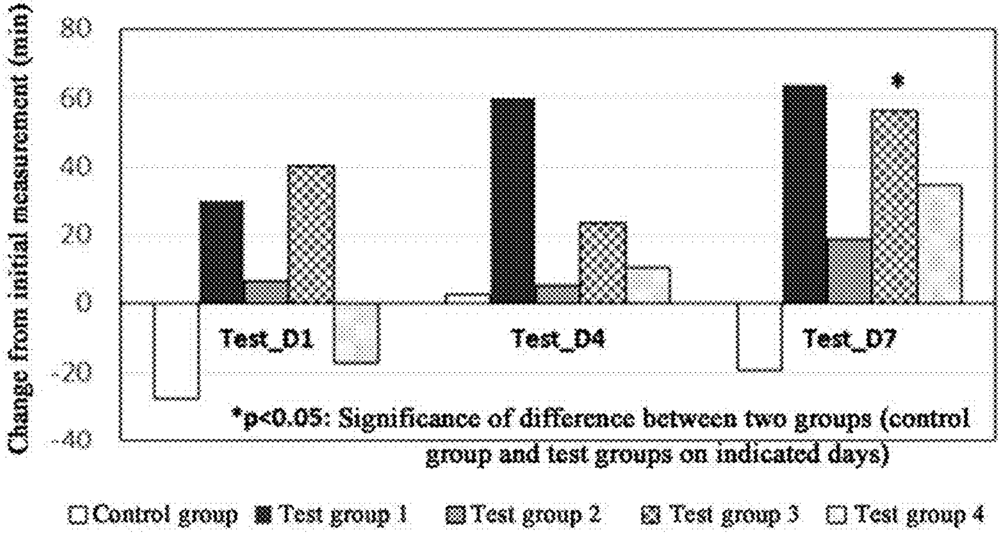
FIG. 4 shows a result of comparing initially measured non-REM sleep time (recorded for 24 hours) and changed non-REM sleep time (recorded for 24 hours) in sleep electroencephalography.

For comparison of the change in sleep quality, the non-REM sleep time, which is a deep sleep state, was analyzed and compared. FIG. 4 shows a result of comparing initially measured non-REM sleep time (recorded for 24 hours) and changed non-REM sleep time (recorded for 24 hours) in sleep electroencephalography. The test group 3 showed significant increase in non-REM sleep time ($p<0.05$) on day 7 after the administration of the microorganisms and the other test groups also showed similar increase patterns, whereas the control group showed slight decrease. In particular, the test group 3 and the test group 1 showed significantly improved sleep quality on day 7 after the administration of the microorganisms, with non-REM sleep time increased by about 1 hour.

Figure 5:
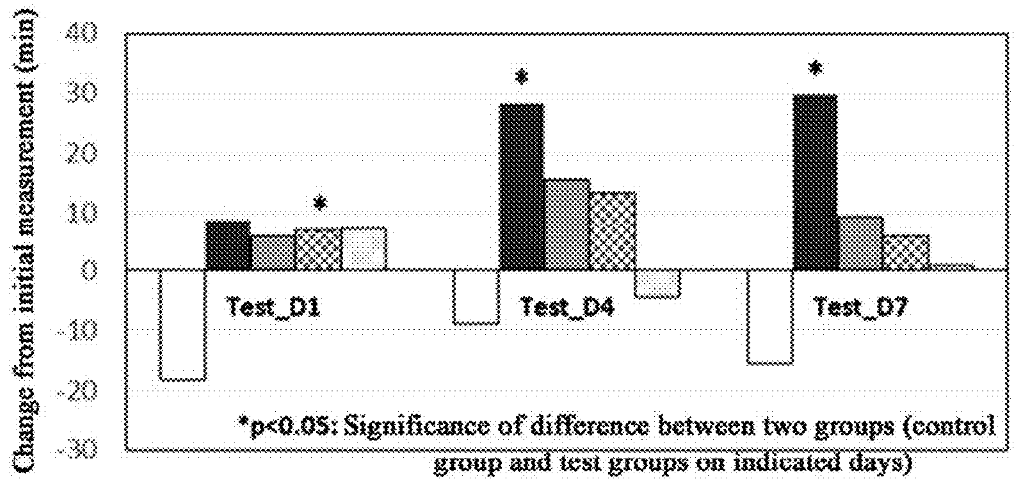
FIG. 5 shows a result of comparing initially measured REM sleep time (recorded for 24 hours) and changed REM sleep time in sleep electroencephalography.

FIG. 5 shows a result of comparing initially measured REM sleep time (recorded for 24 hours) and changed REM sleep time in sleep electroencephalography. The test groups showed overall increase in REM sleep time during the microorganism administration period. In particular, the test group 1 showed increase in REM sleep time by about 30 minutes on days 4 and 7 after the administration of the microorganisms as compared to the control group ($p<0.05$). It was confirmed that the test group 1 which showed the most increase in total sleep time also showed increase in light sleep time.

Figure 6:
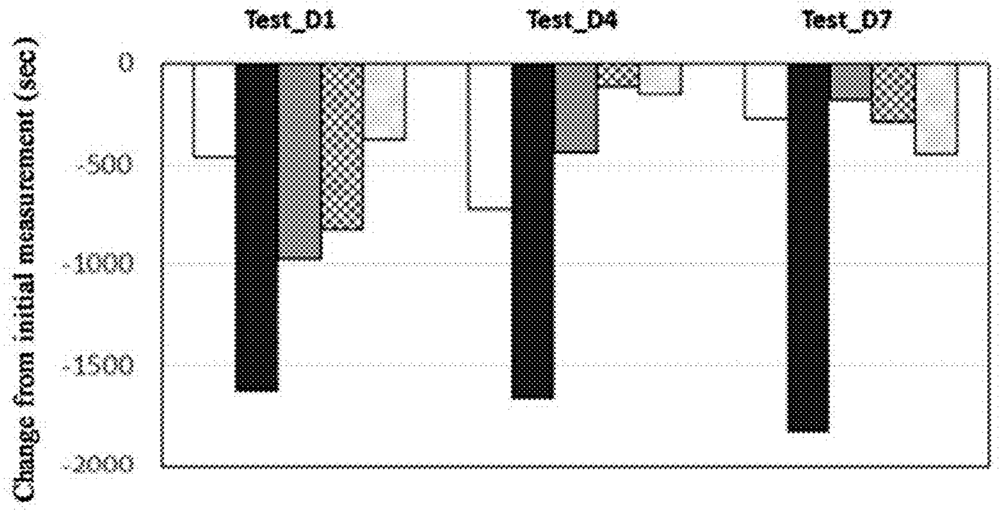
FIG. 6 shows a result of comparing initially measured total sleep latency (length of time to sleep onset) and changed sleep latency (recorded for 24 hours) in sleep electroencephalography.

FIG. 6 shows a result of comparing initially measured total sleep latency (length of time to sleep onset) and changed sleep latency (recorded for 24 hours) in sleep electroencephalography. Although there was no significant difference, sleep latency was decreased in the test group 1 as compared to control group, by about 25 minutes. In addition, the test group 2 and the test group 3 showed decreased sleep latency on the first day of microorganism administration and the test group 4 showed decreased sleep latency on day 7 after the administration of the microorganisms, as compared to the control group.

Figure 7:
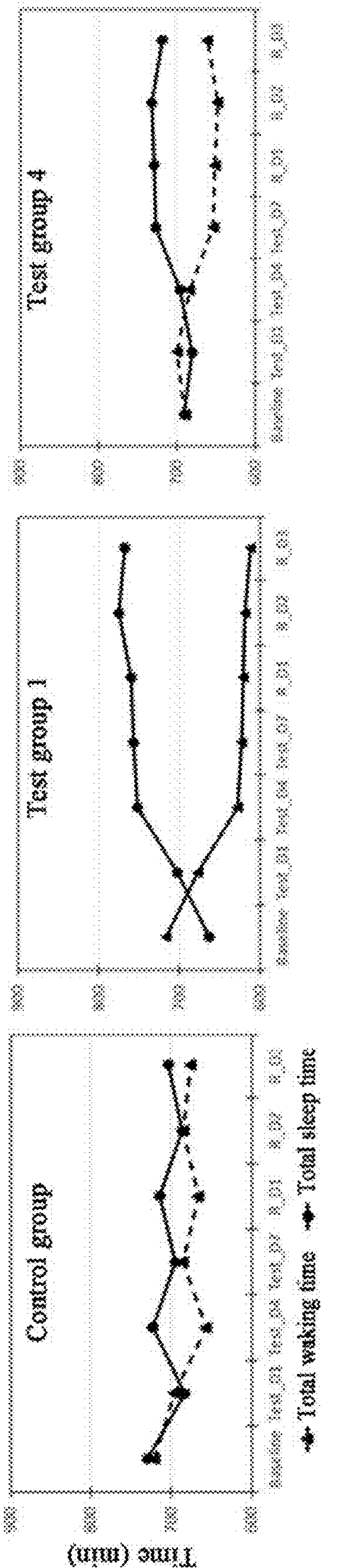
FIG. 7 shows a result of investigating change in initially measured sleep time and waking time (recorded for 24 hours) for a control group, test group 1 and test group 4 in sleep electroencephalography.
Figure 8:
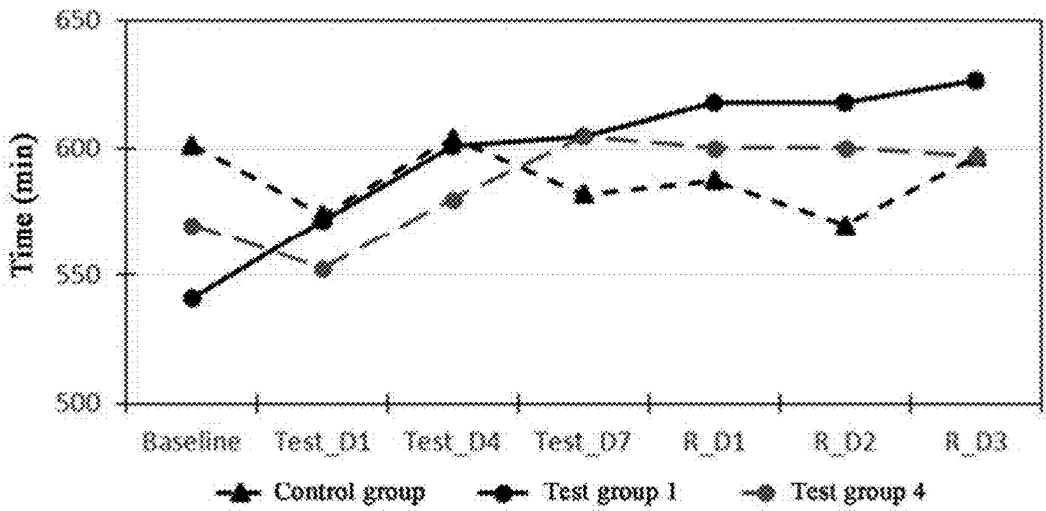
FIG. 8 shows a result of investigating change in non-REM sleep time (recorded for 24 hours) in sleep electroencephalography.

FIGS. 7 and 8 show a result of comparing the sleep measurement values during the administration of the microorganisms and after the stopping of the administration of the microorganisms in sleep electroencephalography for the control group and the test groups (test group 1 and test group 4) with the baseline sleep measurement values through statistical tests.

FIG. 7 shows a result of investigating change in initially measured sleep time and waking time (recorded for 24 hours) for a control group, test group 1 and test group 4 in sleep electroencephalography. For the control group, the total sleep time decreased and increased repeatedly from the first day of the microorganism administration to day 7 after the administration and day 3 after the stopping of the administration, but the finally measured sleep time was almost similar to the initially measured sleep time. However, the test group 1 showed increase in sleep time from the first day of the microorganism administration. The sleep time was increase abruptly on days 4 and 7 and the tendency of increase was maintained until day 3 after the stopping of the administration. The test group 4 also showed increased sleep time on day 7 after the administration of the microorganisms although the increase was less than the test group 1. The tendency of increase was maintained until day 2 after the stopping of the administration but was decreased significantly on day 3. The waking time was also decreased and increased repeatedly for the control group. But, the waking time was steadily decreased by up to about 111 minutes in the test group 1 and up to about 42 minutes in the test group 4. It is considered that the decreased waking time was converted to sleep time.

FIG. 8 shows a result of investigating change in non-REM sleep time (recorded for 24 hours) in sleep electroencephalography. For the control group, the non-REM sleep time decreased and increased repeatedly from the first day of the microorganism administration to day 7 after the administration and the last day after the stopping of the administration, but the finally measured non-REM sleep time was almost similar to the initially measured non-REM sleep time. The test group 1 showed increase in sleep time from the first day of the microorganism administration. It was increased rapidly on day 7 and the tendency of increase was maintained until day 3 after the stopping of the administration. The test group 4 also showed increase in non-REM sleep time until day 7 after the administration of the microorganisms. The degree of increase was similar to the test group 1, but the tendency of increase was maintained longer after the stopping of the administration.

2. Result of Animal Experiments Using Extracellular Vesicles (EVs) of Strains

The sleep electroencephalography results were obtained for all the experimental white rats. The baseline sleep measurement values were measured for 1 day (test group 6) or 2 days (test group 5, the average value was used), and the sleep measurements were recorded on days 1, 3 and 6 after the administration of the EVs. Because the result is limited in terms of statistical significance due to the small number of experimental animals, a distinct tendency in change was observed.

Figure 9:
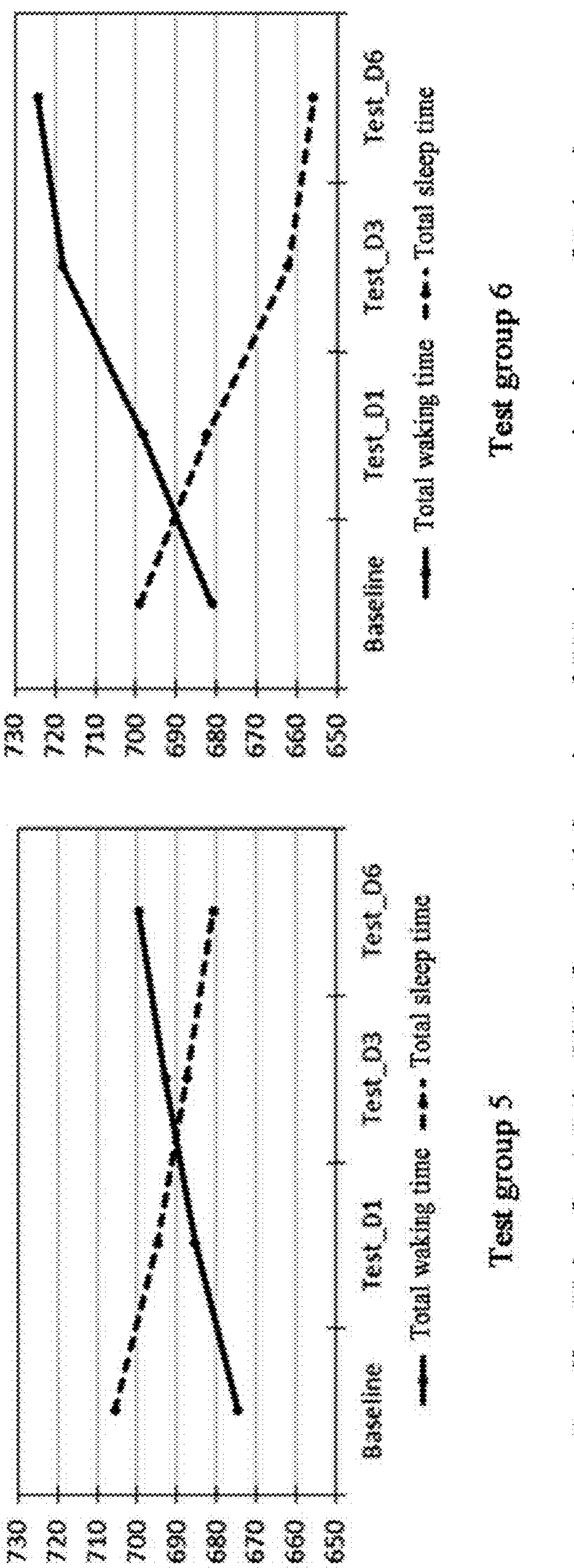
FIG. 9 shows a result of investigating change in measured sleep time and waking time (recorded for 24 hours) in sleep electroencephalography.

FIG. 9 shows a result of investigating change in measured sleep time and waking time (recorded for 24 hours) in sleep electroencephalography. The total sleep time was increased from the first day of the EV administration and increased steadily until days 3 and 6, by about 25 minutes for the test group 5 and by about 43 minutes for the test group 6. In contrast, the waking time was decreased steadily, suggesting that the decreased waking time was converted to sleep time. For the test group 6, although the amount of the EVs was about ½ of the test group 5 as 2 mg, the sleep time was increased by 1.7 times.

Figure 10:
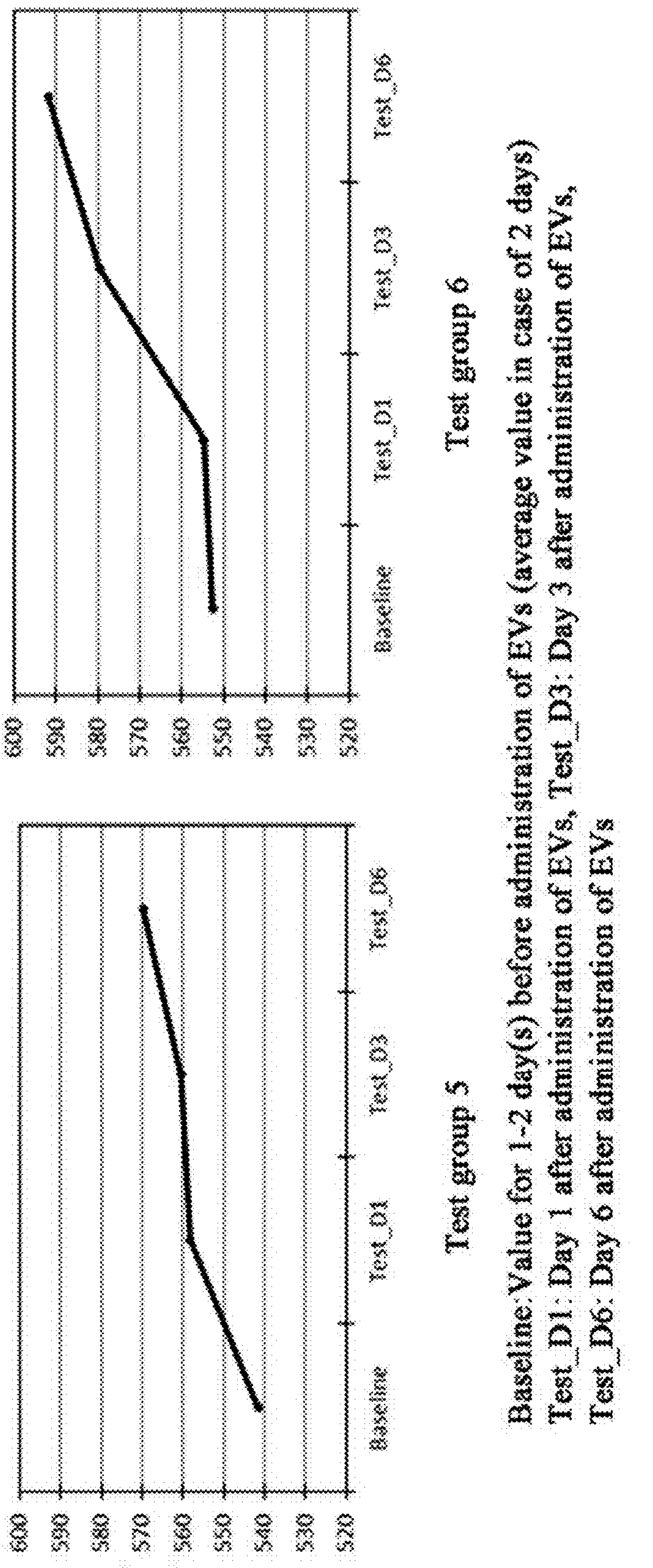
FIG. 10 shows a result of investigating change in measured non-REM sleep time (recorded for 24 hours) in sleep electroencephalography.

FIG. 10 shows a result of investigating change in measured non-REM sleep time (recorded for 24 hours) in sleep electroencephalography. The sleep time was increased from the first day of the EV administration and increased steadily until days 3 and 6. The non-REM sleep time was increased by about 30 minutes for the test group 5 and by about 40 minutes for the test group 6. The increased sleep time observed in FIG. 9 corresponded to the non-REM sleep time.

Although the exemplary embodiments of the present disclosure were described above, those having ordinary knowledge in the art can variously change and modify the present disclosure through addition, change, deletion, etc. without departing from the spirit of the present disclosure described in the claims, which are encompassed in the scope of the present disclosure.

[Accession Number]

Depository agency: the Korean Culture Center of Microorganisms
Accession number: KCCM13103P
Date of deposition: 20220111

Depository agency: the Korean Culture Center of Microorganisms
Accession number: KCCM13104P
Date of deposition: 20220111

Depository agency: the Korean Culture Center of Microorganisms
Accession number: KCCM13105P
Date of deposition: 20220111

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

To. Joong-Ki Kook
College of Dentistry, Chosun University,
309, Pilmun-daero, Dong-gu,
Gwangju 61452,
Republic of Korea RECEIPT IN THE CASE OF AN ORIGINAL DEPOSIT issued pursuant to Rule 7.1 by the INTERNATIONAL DEPOSITARY AUTHORITY identified at the bottom of this page

I. IDENTIFICATION OF THE MICROORGANISM

| Identification reference given by the DEPOSITOR: | Accession number given by the INTERNATIONAL DEPOSITARY AUTHORITY: |
| --- | --- |
| *Prevotella histicola* KCOM 3796 | KCCM13103P |

II. SCIENTIFIC DESCRIPTION AND/OR PROPOSED TAXONOMIC DESIGNATION

The microorganism identified under I above was accompanied by:
☐ a scientific description
☐ a proposed taxonomic designation
(Mark with a cross where applicable)

III. RECEIPT AND ACCEPTANCE

This International Depositary Authority accepts the microorganism identified under I above, which was received by it on January. 11. 2022 (date of the original deposit).[1]

IV. RECEIPT OF REQUEST FOR CONVERSION

The microorganism identified under I above was received by this International Depositary Authority on (date of the original deposit) and a request to convert the original deposit to a deposit under the Budapest Treaty was received by it on (date of receipt of request for conversion).

V. INTERNATIONAL DEPOSITARY AUTHORITY

| Name : Korean Culture Center of Microorganisms<br><br>Address : Yurim B/D<br>45, Hongjenae-2ga-gil<br>Seodaemun-gu<br>SEOUL 03641<br>Republic of Korea | Signature(s) of person(s) having the power to represent the International Depositary Authority or of authorized official(s):<br><br>Date: January. 11. 2022. |
| --- | --- |

[1] Where Rule 6.4(d) applies, such date is the date on which the status of international depositary authority was acquired.

Form BP/4 (sole page)

KOREAN CULTURE CENTER OF MICROORGANISMS

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

To. Joong-Ki Kook
College of Dentistry, Chosun University,
309, Pilmun-daero, Dong-gu,
Gwangju 61452,
Republic of Korea RECEIPT IN THE CASE OF AN ORIGINAL DEPOSIT issued pursuant to Rule 7.1 by the INTERNATIONAL DEPOSITARY AUTHORITY identified at the bottom of this page

I. IDENTIFICATION OF THE MICROORGANISM

Identification reference given by the DEPOSITOR: *Prevotella histicola* KCOM 3081

Accession number given by the INTERNATIONAL DEPOSITARY AUTHORITY: KCCM13404P

II. SCIENTIFIC DESCRIPTION AND/OR PROPOSED TAXONOMIC DESIGNATION

The microorganism identified under I above was accompanied by:
☐ a scientific description
☐ a proposed taxonomic designation
(Mark with a cross where applicable)

III. RECEIPT AND ACCEPTANCE

This International Depositary Authority accepts the microorganism identified under I above, which was received by it on January. 11. 2022 (date of the original deposit).[1]

IV. RECEIPT OF REQUEST FOR CONVERSION

The microorganism identified under I above was received by this International Depositary Authority on (date of the original deposit) and a request to convert the original deposit to a deposit under the Budapest Treaty was received by it on (date of receipt of request for conversion).

V. INTERNATIONAL DEPOSITARY AUTHORITY

Name : Korean Culture Center of Microorganisms

Address : Yurim B/D
45, Hongjenae-2ga-gil
Seodaemun-gu
SEOUL 03641
Republic of Korea Signature(s) of person(s) having the power to represent the International Depositary Authority or of authorized official(s):

Date: January. 11. 2022.

[1] Where Rule 6.4(d) applies, such date is the date on which the status of international depositary authority was acquired.

Form BP/4 (sole page)

KOREAN CULTURE CENTER OF MICROORGANISMS

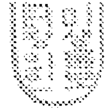

BUDAPEST TREATY ON THE INTERNATIONAL RECOGNITION OF THE DEPOSIT OF MICROORGANISMS FOR THE PURPOSES OF PATENT PROCEDURE

INTERNATIONAL FORM

To. Joong-Ki Kook
College of Dentistry, Chosun University,
309, Pilmun-daero, Dong-gu,
Gwangju 61452,
Republic of Korea RECEIPT IN THE CASE OF AN ORIGINAL DEPOSIT issued pursuant to Rule 7.1 by the INTERNATIONAL DEPOSITARY AUTHORITY identified at the bottom of this page

I. IDENTIFICATION OF THE MICROORGANISM

| Identification reference given by the DEPOSITOR: | Accession number given by the INTERNATIONAL DEPOSITARY AUTHORITY: |
|---|---|
| *Prevotella histicola* KCOM 3227 | KCCM13105P |

II. SCIENTIFIC DESCRIPTION AND/OR PROPOSED TAXONOMIC DESIGNATION

The microorganism identified under I above was accompanied by:
☐ a scientific description
☐ a proposed taxonomic designation
(Mark with a cross where applicable)

III. RECEIPT AND ACCEPTANCE

This International Depositary Authority accepts the microorganism identified under I above, which was received by it on January. 11. 2022 (date of the original deposit).[1]

IV. RECEIPT OF REQUEST FOR CONVERSION

The microorganism identified under I above was received by this International Depositary Authority on (date of the original deposit) and a request to convert the original deposit to a deposit under the Budapest Treaty was received by it on (date of receipt of request for conversion)

V. INTERNATIONAL DEPOSITARY AUTHORITY

| Name : Korean Culture Center of Microorganisms<br>Address : Yurim B/D<br>45, Hongjenae-2ga-gil<br>Seodaemun-gu<br>SEOUL 03641<br>Republic of Korea | Signature(s) of person(s) having the power to represent the International Depositary Authority or of authorized official(s):<br>Date: January. 11. 2022. |
|---|---|

[1] Where Rule 6.4(d) applies, such date is the date on which the status of international depositary authority was acquired.

Form BP/4 (sole page)

The invention claimed is:

1. A method for alleviating or treating sleep disorder, comprising administering a therapeutically effective amount of a composition comprising *Prevotella histicola*, a culture product thereof, a crushed product thereof, an extract thereof or a fermented product thereof; or extracellular vesicles derived from *Prevotella histicola* to a subject in need thereof, wherein the sleep disorder is one or more selected from a group consisting of insomnia, breathing-related sleep disorder and circadian rhythm sleep disorder.

2. The method according to claim 1, wherein the insomnia is one or more selected from a group consisting of sleep onset insomnia, sleep maintenance insomnia and sleep terminal insomnia.

3. The method according to claim 1, wherein the breathing-related sleep disorder is one or more selected from a group consisting of obstructive sleep apnea syndrome, central sleep apnea syndrome and central alveolar hypoventilation syndrome.

4. The method according to claim 1, wherein the circadian rhythm sleep disorder is one or more selected from a group consisting of a delayed sleep phase type, an advanced sleep phase type, a jet lag type and a shift work type.

5. The method according to claim 1, wherein the sleep disorder is prevented or treated by increasing total sleep time.

6. The method according to claim 1, wherein the sleep disorder is prevented or treated by increasing non-REM (NREM) sleep time.

7. The method according to claim 1, wherein the sleep disorder is prevented or treated by increasing REM sleep time.

8. The method according to claim 1, wherein the sleep disorder is prevented or treated by decreasing sleep latency.

9. The method according to claim 1, wherein the sleep disorder is prevented or treated by decreasing total waking time.

10. The method according to claim 1, wherein the culture, lysate, extract or fermentation product of *Prevotella histicola* comprises the extracellular vesicles of *Prevotella histicola*.

11. The method according to claim 1, wherein the extracellular vesicles have a size of 10-600 nm.

12. The method according to claim 1, wherein the *Prevotella histicola* is *Prevotella histicola* with an accession number selected from a group consisting of KCTC 15171, CCUG 55407, DSM 19854, JCM 15637, CCUG 60372, KCCM13103P, KCCM13104P and KCCM13105P.

13. The method according to claim 1, wherein the composition is a pharmaceutical composition.

14. A method for preparing a composition for alleviating or treating sleep disorder, comprising a step of preparing extracellular vesicles derived from a *Prevotella histicola* strain, wherein the sleep disorder is one or more selected from a group consisting of insomnia, breathing-related sleep disorder and circadian rhythm sleep disorder.

* * * * *